(12) United States Patent
Causton et al.

(10) Patent No.: US 6,287,035 B1
(45) Date of Patent: Sep. 11, 2001

(54) FLUID DISPENSATION

(75) Inventors: Brian Edward Causton; Dawn Elizabeth Ann Gough, both of Reading (GB)

(73) Assignee: Berol Corporation, Freeport, IL (US)

( * ) Notice: Subject to any disclaimer, the term of this patent is extended or adjusted under 35 U.S.C. 154(b) by 0 days.

(21) Appl. No.: 09/481,287

(22) Filed: Jan. 11, 2000

Related U.S. Application Data (63) Continuation of application No. PCT/GB98/02095, filed on Jul. 16, 1998.

(30) Foreign Application Priority Data

Jul. 17, 1997 (GB) .................................................. 9715123

(51) Int. Cl.⁷ ................................................. A46B 5/02
(52) U.S. Cl. ...................... 401/190; 401/222; 222/386.5; 222/399
(58) Field of Search ............................ 401/190, 188 R, 401/188 A, 222, 232; 222/386.5, 394, 399

(56) References Cited

U.S. PATENT DOCUMENTS

| | | | |
|---|---|---|---|
| 3,000,354 | * 9/1961 | Germann | 401/133 A |
| 3,115,868 | * 12/1963 | De Molin et al. | 401/188 R |
| 3,130,711 | * 4/1964 | Eckerle | 401/188 R |
| 3,144,005 | 8/1964 | Johmann . | |
| 3,164,132 | 1/1965 | Ganz et al. . | |
| 3,192,904 | 7/1965 | Johmann . | |
| 3,326,189 | 6/1967 | Baer et al. . | |
| 3,705,855 | 12/1972 | Marschner | 252/90 |
| 3,797,945 | 3/1974 | Zepell . | |
| 3,819,282 | 6/1974 | Schultz . | |
| 5,279,819 | 1/1994 | Hayes | 424/73 |
| 5,423,454 | * 6/1995 | Lippman et al. | 222/1 |
| 5,601,376 | 2/1997 | Badr et al. . | |
| 5,871,296 | 2/1999 | Furukawa et al. . | |
| 5,915,866 | 6/1999 | Furukawa . | |
| 5,918,993 | 7/1999 | Koyama . | |

FOREIGN PATENT DOCUMENTS

| | | | |
|---|---|---|---|
| 43 09 770 A1 | 9/1993 | (DE) | B43K/7/02 |
| 4309770 | 9/1993 | (DE) . | |
| 346 289 | * 12/1989 | (EP) | 222/386.5 |
| 2 097 007 | 10/1982 | (GB) | C09D/3/48 |
| 2097007 | 10/1982 | (GB) . | |
| 2 166 150A | 4/1986 | (GB) | C11D/10/04 |
| 2166150 | 4/1986 | (GB) . | |
| 02036294 | 2/1990 | (JP) . | |
| 2036294 | 2/1990 | (JP) | A61K/7/06 |
| 8-164696 | 6/1996 | (JP) . | |
| 10264584 | 10/1998 | (JP) . | |
| 9216188 | 10/1992 | (WO) . | |
| WO 92/16188 | 10/1992 | (WO) | A61K/7/15 |

OTHER PUBLICATIONS

Derwent Abstract of JP 02036294 dated Feb. 6, 1990 (XP–002080874).

* cited by examiner

*Primary Examiner*—David J. Walczak
(74) *Attorney, Agent, or Firm*—Marshall, O'Toole, Gerstein, Murray & Borun (57) ABSTRACT

Pressure generating gas-releasing compositions which are microemulsions, siloxane or hydrocarbon greases or elastomers, are used to aid dispensation of a fluid from a reservoir without the composition itself being dispensed. Dispensers containing such compositions can include writing implements.

43 Claims, 3 Drawing Sheets

FLUID DISPENSATION

This application is a continuation of copending application International Application PCT/GB98/02095 filed on Jul. 16, 1998 and which designated the U.S., claims the benefit thereof and incorporates the same by reference.

BACKGROUND OF THE INVENTION

1. Field of the Invention

This invention relates to the dispensation of fluids from a reservoir and particularly, but not exclusively, to the dispensation of ink in writing implements.

2. Description of Related Technology

There are a number of conventional techniques for delivering ink from an ink reservoir to the tip of a pen. The simplest technique is to rely on a gravity feed; however, this will not work well, and may not work at all, if the pen is turned upside down or if the ink is too viscous.

Another technique is to use a pressurised permanent gas, such as nitrogen, within the ink reservoir. The gas ensures that a sufficient pressure is maintained on the ink to push it towards the tip of the pen. However, there is a problem with this technique: as the ink is dispensed from the reservoir, the pressure in the reservoir drops, because there is a greater volume for the gas to occupy. In order to overcome this problem, the gas must be provided initially at high pressure, and must occupy a large part of the volume of the reservoir relative to the ink: in practice, up to 90% of the volume of the reservoir may initially be occupied by gas.

SUMMARY OF THE INVENTION

We have now found that the problems described above can be overcome and that fluids can advantageously be dispensed from a reservoir by using a pressure generating composition capable of releasing a volatile component, wherein the volatile component is released from the composition as the fluid is dispensed in order to maintain the pressure in the reservoir at a level sufficient to aid dispensation of the fluid, the pressure generating composition itself remaining in the reservoir and not being dispensed with the fluid.

According to one aspect of the invention, therefore, there is provided the use of a pressure generating composition capable of releasing a volatile component to generate a pressure, to aid the dispensation of a fluid from a reservoir without the said composition itself being dispensed, wherein the pressure generating composition comprises an oil-in-water or water-in-oil microemulsion, or a siloxane or hydrocarbon grease, or an elastomer, containing said volatile component.

The invention is particularly suitable for dispensing inks from a pen, but can be used for dispensing other fluids from containers thereof.

According to another aspect, the invention provides a dispenser for dispensing a fluid, which dispenser comprises a reservoir containing said fluid, the reservoir having an outlet through which said fluid can be dispensed, and a pressure generating composition capable of releasing a volatile component to generate a pressure within the reservoir to aid dispensation of the fluid, wherein said composition is capable of releasing the volatile component as the fluid is dispensed, in order to maintain the pressure in the reservoir at a level sufficient to aid dispensation of the fluid, and wherein the said composition is not dispensed with the fluid, said pressure generating composition comprising water-in-oil or oil-in-water a microemulsion or a siloxane or hydrocarbon grease, or an elastomer, containing said volatile component.

DETAILED DESCRIPTION OF THE INVENTION

The fluid can be any flowable material, but the invention is particularly suitable for aiding the dispensation of viscous fluids that do not flow well under the influence of gravity. For example, dispensation of pastes such as toothpaste and the like, and gels such as deodorant- or antiperspirant-containing gels and the like, or wet shaving preparations such as soaps and shaving aids, can be assisted by the present invention. The invention is particularly (but not exclusively) useful for aiding the dispensation of fluid from writing or correction instruments, particularly such fluids which are viscous, e.g. inks as used in ballpoint pens and the like. The invention is also useful to aid in the dispensation of solvent and water-based inks.

The pressure necessary to aid dispensation of the fluid from the reservoir depends upon a number of factors, such as the properties of the fluid, and the size and shape of the reservoir. A reservoir pressure above about 0.5 psi (3.4 kPa), preferably above about 1 psi (6.89 kPa), is normally sufficient to aid dispensation of the fluid. The maximum reservoir pressure is dictated by the strength of the reservoir and the characteristics of the pressure generating composition. Generally, the pressure will not be greater than 60 psi (413 kPa), preferably from 1 to 15 psi (6.9 to 103 kPa). In practice, it would not normally be necessary for the maximum reservoir pressure to be above about 10 psi (68.9 kPa). For most dispensers, the reservoir pressure is preferably in the range 1 to 4 psi (6.9 to 27.6 kPa). However, the optimum conditions will depend on all the circumstances and can be determined in any particular case by routine trial and experiment.

It will be understood that generally the pressure generating composition is not itself dispensed with the fluid from the reservoir. Rather, the composition remains in the reservoir as the fluid is dispensed, the composition serving to maintain a gas pressure to aid in dispensing the fluid. Thus, the pressure generating composition is normally used in a way in which it does not intimately mix with the fluid to be dispensed, although it may be in direct contact therewith at an interface.

Ideally, the pressure generating composition should be immiscible with the liquid to be dispensed. For example, if the fluid to be dispensed is organic-based, then the pressure generating material should be aqueous-based; and if the fluid to be dispensed is aqueous-based, then the pressure generating material should be organic-based. Alternatively, a barrier may be provided between the fluid to be dispensed and the pressure generating material, in order to prevent contact therebetween especially when both are organic-based or aqueous-based. For example, in the case of an aqueous-based fluid and an aqueous pressure generating material, an organic-based barrier, such as a grease plug, can be provided between the fluid and the pressure generating material. The use of a barrier can be very important when dispensing low viscosity fluids, in order to prevent the formation of air bubbles.

Over a period of time, it is possible for the fluid being dispensed, or for the barrier, to dissolve some of the volatile component from the atmosphere in the reservoir. This does not normally affect the operation of the invention although preferably the barrier material will be such as not to dissolve the volatile component to any significant extent.

Another way of providing a barrier between the pressure generating composition and the fluid to be dispensed is to confine the composition in an expandable bladder, bag or other flexible container, for example, the container being disposed within the reservoir containing the fluid to be dispensed. As the composition releases the volatile component, the container expands to raise the pressure in the reservoir to aid dispensation of the fluid.

In one preferred embodiment of the invention, the fluid is an ink, and the fluid dispenser is part of a writing implement having a tip for delivering the ink to a surface to be written on, or otherwise marked. In this embodiment, the reservoir and the tip are in fluid communication, whereby ink can be fed from the reservoir to the tip.

In another embodiment, the fluid is an ink, and the fluid dispenser comprises a refill for a writing implement. The ink may be a water-based or solvent-based ink and may be for use in ballpoint pens or other writing instruments.

In further exemplary embodiments, the fluid is a paste such as toothpaste, or a gel material, or a fluid such as a correction fluid or shaving soap or a shaving aid.

In use of the pressure generating compositions in the present invention, the compositions release a volatile component at ambient temperatures. In some embodiments, at least some of the volatile component will be in solution in a component of the composition, or it may be otherwise dispersed in the composition. In accordance with a feature of the invention, we prefer to use as pressure generating compositions in the invention, stabilised oil-in-water or water-in-oil microemulsions in which the oil phase acts as a reservoir for the volatile component. Examples of such compositions are known (but are used for quite different purposes from the present invention) and are described, for example, in U.S. Pat. No. 3,541,581. In U.S. Pat No. 3,541,581, the microemulsion is in the form of a stable post-forming gel comprising water, a soap, a volatile liquid, and a water-soluble gelling agent. The gel is stored in a container and, when dispensed, the volatile liquid therein evaporates and, as a result, the gel becomes foamed. The composition is useful as a personal care lather-producing soap composition.

For use in the present invention, such microemulsions need to be formulated to give the desired pressure-generation effect and this will be within the skill of those skilled in the art, using routine trial and experiment to determine the optimum conditions in any particular case. Most preferably, the microemulsions are so formulated as to be of gel-like consistency, normally having a viscosity in the range 200 to 20,000 centipoise (cP). By "microemulsion", we mean an emulsion in which the disperse phase is of a diameter of less than about 0.05 micrometer.

For the aqueous phase of the microemulsions, we prefer to use an aqueous soap solution (or the like). The soap is preferably the reaction product of a fatty acid and a metal compound or an amine. The metal compound is suitably a metal hydroxide. The metal of the metal compound may be, for example, an alkali metal, such as Li, Na or K, or an alkaline earth metal, such as Mg or Ca. The amine compound is preferably triethanolamine, monoethanolamine, diethanolamine, isopropanolamine, aminomethylpropanol, aminomethylpropane diol, or another organic amine. The fatty acid desirably has from 8 to 18, more desirably from 10 to 16, carbon atoms. Palmitic acid and lauric acid are particularly preferred fatty acids.

The soap may be formed, for example, from 60 to 80 wt % fatty acid, preferably 65 to 75 wt % fatty acid. The aqueous soap solution typically contains 50 to 75 wt % water, preferably 65 to 75 wt % water.

Instead of soaps, sarcosinates can be used. Examples are crodasinic O,L,M and C available from Croda Chemicals Ltd., Hull, England, and Hampsoyl L95,L,M,C,O and S from Hampshire Chemicals Ltd.

The oil phase of the microemulsion is insoluble in the aqueous phase, eg. soap solution, and is preferably a mineral oil, corn oil, isopropyl myristate, dimethyl siloxane (or polydimethyl siloxane), isocetyl alcohol, lauryl lactate, or a synthetic oil such as polydecane, polyhexane or polyisobutane, or polybutene. We especially prefer the use of a mineral oil.

Instead of using microemulsions, simple solutions or dispersions of a volatile component in a material may be used, such as in an elastomer, eg. polyisobutylene of molecular weight below about 4000. Also, it is possible to use greases to contain the volatile component and so form pressure generating compositions for use in the invention. Thus, in oil-containing greases such as Gilugel, the oil can act as a reservoir for the pressure generating agent. Examples of oils which can be used in this way are mineral oil, isopropyl myristate, isopropyl palmitate, cyclomethicone pentamer and castor oil.

Advantageously, the volatile component in the pressure generating compositions will be at least partly soluble in any oil or aqueous phase of the compositions at 25° C. It is especially preferred that the volatile component is a non-permanent gas. The volatile component preferably has a vapour pressure of 8 to 40 psi (55 to 276 kPa) at 25° C. The boiling point of the volatile component is preferably in the range 30 to 36° C. Suitable volatile components include saturated aliphatic hydrocarbons, having 4 to 6 carbon atoms, and partially or wholly halogenated hydrocarbons. It is possible to use a mixture of two or more volatile components in a the pressure generating composition. One particularly suitable volatile component is isopentane which provides a pressure of 4.5 to 5.7 psi (31 to 39 kPa). A 25:75 blend of isobutane and isopentane gives a pressure of 10.5 to 11.0 psi (72 to 76 kPa).

One preferred form of the pressure generating microemulsion composition with the volatile component dissolved therein comprises:

Water: 50–70 wt %

Soap: 20–40 wt %

Organic liquid: 5–20 wt %

Volatile component: 1–10 wt %

Additives: 0–10 wt %

Among the additives which may be present are lauryl alcohol, cetyl alcohol, stearyl alcohol, Clarit PDP-200 (Pentadoxynol-200), propylene glycol, and preservatives such as methyl paraben and propyl paraben.

A more preferred form of the pressure generating composition comprises:

Water: 55–65 wt %

Soap: 25–35 wt %

Organic liquid: 5–10 wt %

Volatile component: 3–5 wt %

Additives: 0–10 wt %

The amounts of each component should be selected, within the above ranges, so that the total is 100 wt %.

The use of pressure generating compositions in accordance with the present invention makes it possible to dispense fluids reliably from a reservoir without the need for a high pressure permanent gas. This enables the reservoir to be manufactured more cheaply, because it does not need to withstand such high pressures. In addition, the reservoir does not need to be pressurised during the manufacturing process: the fluid and the pressure generating material can be placed in the reservoir at atmospheric pressure, using conventional manufacturing methods, and then the reservoir can be sealed. After sealing, the reservoir pressure will build up, over time, to the required working pressure as the pressure generating material releases gas into the reservoir. Whilst the actual time will depend on all the circumstances, it will normally only be a matter of minutes, e.g. from 8 to 12 minutes.

The ability of the pressure generating composition to release gas, in order to maintain a sufficient pressure within the reservoir, makes it possible to provide much more fluid in the reservoir than would be possible with the use of a pressurised permanent gas. For example, when the invention is applied to a writing implement, 80% of the volume of the reservoir may be occupied by ink and 5% occupied by the pressure generating material.

Reference is now made to the accompanying drawings, wherein.

Figure 1:
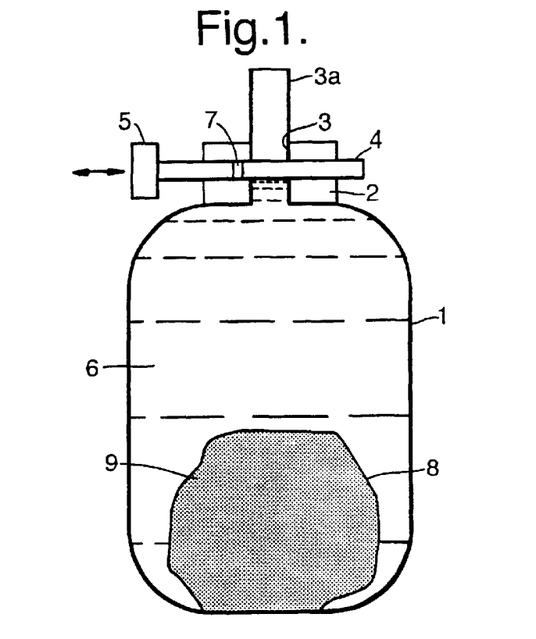
FIG. 1 is a diagrammatic cross-sectional view of a valved fluid reservoir containing an expansible container with a pressure generating composition therein.
Figure 2:
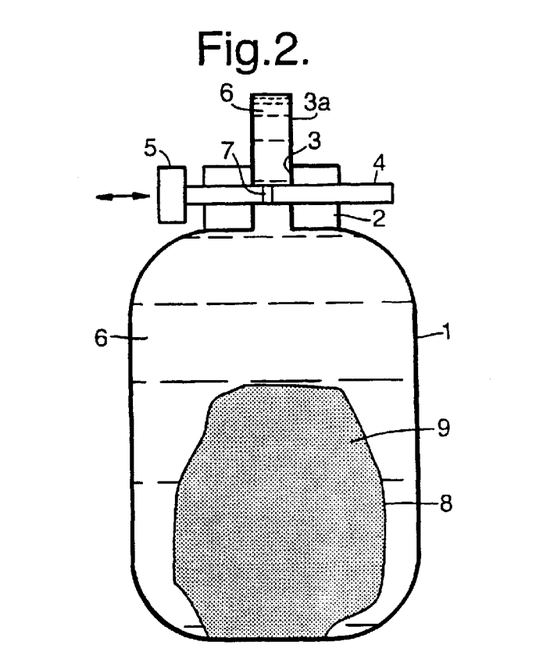
FIG. 2 is the same as FIG. 1 except that some fluid has been dispensed from the reservoir.

Referring to FIGS. 1 and 2, there is shown schematically a reservoir vessel 1 having a neck portion 2 in which is formed an outlet passage 3 connecting to an outlet tube 3a. The outlet passage 3 is normally closed (FIG. 1) by a valve member 4. Valve member 4 has an operating button 5 by which it can be moved to bring an orifice 7 in the member into alignment with outlet passage 3 (see FIG. 2) to allow fluid 6 in the vessel 1 to pass out of the vessel. The valve member may be spring-biased so as to return to the closed position when pressure on the operating button 5 is released.

Within vessel 1 is an expansible closed container 8 immersed in fluid 6. Within container 8 out of direct contact with fluid 6 is a pressure generating composition. In use, the composition releases a gas 9 within the container 8 and the container expands until the gas pressure within it is exactly balanced by the fluid pressure in vessel 1. The fluid in vessel 1 is thus pressurised so that, when valve member 4 is moved to the open position (FIG. 2), the fluid is driven out of vessel 1 through outlet passage 3 and outlet tube 3a.

When a quantity of fluid 6 is dispensed from reservoir vessel 1, the pressure in the fluid 6 in vessel 1 is lower than it was immediately prior to the dispensing. As a result, the pressure generating composition in container 8 releases more gas so that container 8 expands (see FIG. 2) until the fluid 6 is again at the same pressure as the gas 9 in container 8. Thus, the pressure in vessel 1 is regenerated ready for dispensing more fluid when valve member 4 is moved to the open position.

As will be clear to those skilled in the art, there are many uses for such a system. One such use is to provide soap or another shaving aid fluid to the blade, for example, of a wet shaving system.

Figure 3:
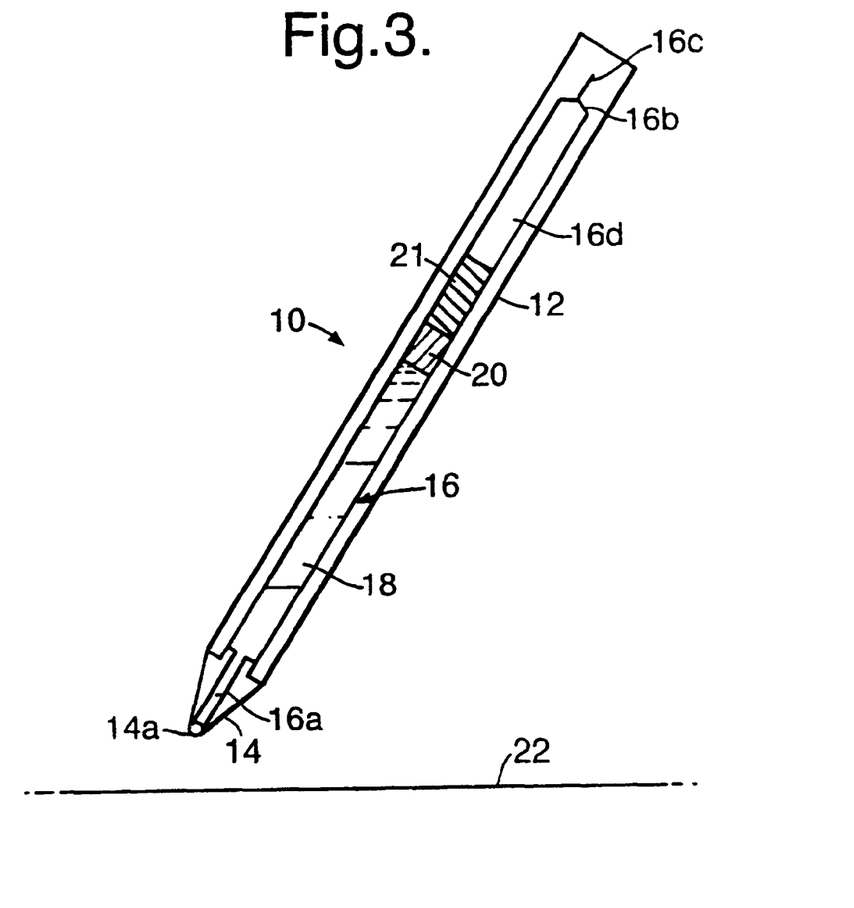
FIG. 3 is a diagrammatic cross-sectional view of an embodiment of a writing implement incorporating a fluid dispenser according to the invention.

Referring to FIG. 3, a writing implement is generally designated 10. The writing implement 10 comprises a housing 12, a tip 14 and a liquid dispenser in the form of a reservoir 16, which is disposed within the housing 12. The reservoir 16 contains an ink 18, and a plug 21 of a pressure generating composition. As illustrated, there is also a barrier plug 20 separating the ink 18 from the plug 21. A barrier plug 20 will normally only be present when the ink 18 and the pressure generating plug 21 are both aqueous based or organic based.

The pressure generating composition comprises a volatile component that can be released, eg. can evaporate, from the pressure generating composition at room temperature.

Outlet passage 16a passes axially through tip 14 communicating reservoir 16 with a ball 14a so that the ink 18 can flow from the reservoir to the ball 14a. Ball 14a is adapted to be brought into contact with a surface 22, such as a sheet of paper, in order to write on, or otherwise mark, the surface 22. The structure of the illustrated tip 14 is entirely conventional. Other such tips include, for example, those which are connected to the reservoir via a valve, eg. a diaphragm valve.

An end 16b of the reservoir 16, which is opposite to the tip 14, is provided with a crimp 16c; the crimp 16c provides the reservoir 16 with an air-tight seal. During manufacture of the liquid dispenser, the ink 18 and the plugs 20 and 21 are placed in the reservoir 16, at atmospheric pressure, then the end 16b is crimped to provide the crimp 16c. (Reservoir 16 can be sealed in other ways, for example by use of a plug.)

There is a volume 16d within the reservoir 16, between the plug 21 and the end 16b of the reservoir 16. The volume 16d contains a gas which has been released from the pressure generating composition 21; the gas in the volume 16d is typically at a pressure of 1 to 4 psig (105 to 129 kPa). The pressure of the gas in the volume 16d pushes plug 21 and the ink 18 towards the outlet 16a. This aids the dispensation of the ink 18 to the ball 14a, and from the roller-ball 14a to the surface 22.

As the ink 18 is dispensed from the reservoir 16, the volume 16d becomes larger. At the same time more of the volatile component is released from the composition, in order to maintain the pressure within the reservoir 16 at a level sufficient to aid the dispensation of the ink 18.

The reservoir 16, tip 14 and the contents 18,21 and (if present) 20, constitute a refill for the writing implement, and can be made and sold for insertion in a housing 12.

It will be appreciated by the skilled person that modifications may be made to the writing implement described above. For example, the writing implement may be provided with many different types of tip, and may have means other than a roller-ball to deliver the ink to the surface. Furthermore, the end of the reservoir remote from the outlet may be sealed by any conventional means.

In order that the invention may be more fully understood, the following Examples of pressure generating compositions, and of their preparation and use, are given by way of illustration only.

EXAMPLE 1

A composition was made of the following components:

|  | wt. % |
|---|---|
| Palmitic acid | 10.57 |
| Triethanolamine | 7.69 |
| Coconut fatty acid | 7.5 |
| Mineral oil | 6 |
| Propylene glycol | 4.11 |
| Isopentane | 4 |
| Methyl paraben | 0.2 |
| Propyl paraben | 0.1 |
| Water | 59.8 |

The water used in the composition was first heated to 95° C. to remove air therefrom.

All the fatty acids and the propylene glycol, methyl paraben, propyl paraben and water were placed in a vessel and heated with stirring under a vacuum to 75° C. With the mixture at this temperature, the triethanolamine was added and the stirring continued. The mixture became viscous as the soap formed, and was allowed to cool. When it reached 20° C., the isopentane and mineral oil were added. Cooling was continued to 10° C. with slow stirring. The resulting gel was stored below 10° C. until required for use.

Further compositions were made in which the amount of mineral oil was varied up to 16% and the amount of isopentane was varied up to 10%, the volume of water being adjusted accordingly q.s. 100%.

All the compositions were very satisfactory as pressure generators when confined in a closed space and allowed to warm to ambient temperature (e.g. about 20° to 25° C.). In particular, they were satisfactory when used as small plugs in ballpoint pen ink reservoirs, above the ink column, the end of the reservoir being closed, as described elsewhere herein.

EXAMPLE 2

A composition was made of the formulation given in Example 1 except that it contained 8.25 wt. % lauric acid in place of the 10.57 wt. % palmitic acid, and 3 wt % isopentane instead of 4 wt. %, and the amount of water was correspondingly 63.15 wt. %.

The composition was made in the same way as that of Example 1.

Further compositions, in which the amount of mineral oil was varied up to 16% and the amount of isopentane was varied up to 10%, the volume of water being adjusted accordingly q.s. 100%, were also made.

All the compositions were very satisfactory as pressure generators when confined in a closed space and allowed to warm to ambient temperature. Like the Example 1 compositions, they were useful in ballpoint pens as described.

EXAMPLE 3

A ballpoint pen ink was made from:
Papermate blue ballpen ink (28.8 g) from Formalals Iberica
2-Phenoxyethanol >99% (3.00 g) from Fluka
Gilugel MIN (6.90 g) from Giuline Chemie GmbH.
The ink was placed in a 50 ml beaker and the 2-phenoxyethanol was added. An Ultra-Turrax T25 mixer was lowered into the beaker to just above the bottom. Thin plastic film was wrapped around the beaker and the stirrer to reduce evaporation, and the mixture was stirred at 8000 rpm for one hour. During this time, the mixture became warm.

At the end of the one hour, the Gilugel MIN was added and the mixture stirred at the same speed for a further 4 hours to form the ballpoint pen ink.

A reservoir tube was filled with ink (about 1 ml) by syringing air from one end of the tube. The tube was then centrifuged at 7.5 cm from centre at 4600 rpm for 10 minutes to remove any entrapped air. Then, a ballpoint was firmly attached to one end of the tube and a quantity (about 1.5 cm in length) of a pressure generating composition according to the present invention was into the open end of the tube. Finally, the open end of the tube was firmly closed with a size 5 bung.

In use of the pen, the ink flowed very smoothly and provided excellent lay down, even when used upside down, without any discontinuity in the writing.

The pressure generating composition was made up of:

| | |
|---|---|
| Hampsoyl L | 11.16% |
| Coconut fatty acid | 7.5% |
| PEG 150 distearate | 0.1% |
| Triethanolamine | 7.69% |
| Empilan MAA | 2.0% |
| Propylene glycol | 4.11% |
| Isopentane | 3.0% |
| Methyl paraben | 0.2% |
| Propyl paraben | 0.1% |
| Mineral oil | 6.0% |
| Water | q.s. 100% |

The pressure generated from this formulation was 4.8 psi.

The water used in this composition was heated to 95° C. to remove air therefrom. The Hampsoyl L, coconut fatty acid, propylene glycol, peg-150-distearate, methyl paraben, propyl paraben and water were placed in a vessel and heated with stirring under vacuum to 75° C. With the mixture at this temperature, the triethanolamine was added and the stirring continued. The mixture became viscous as the soap formed, and was allowed to cool. When it reached 10° C., the isopentane and mineral oil were added. The resulting gel was then stored at 4° C. until required for use.

EXAMPLE 4

The following microemulsion was made by the procedure of Example 1. It had a soap content of approximately 40%.

| Material | % w/w |
|---|---|
| Water | 33.97 |
| Palmitic acid | 21.14 |
| Triethanolamine | 15.38 |
| Coconut fatty acid | 15 |
| Mineral oil | 6 |
| Propylene glycol | 4.11 |
| Isopentane | 4 |
| Methyl paraben | 0.2 |
| Propyl paraben | 0.1 |
| Peg-150-distearate | 0.1 |

The water used in this composition was heated to 95° C. to remove air therefrom. All the fatty acids, propylene glycol, peg-150-distearate, methyl paraben, propyl paraben and water were placed in a vessel and heated with stirring under vacuum to 75° C. With the mixture at this temperature, the triethanolamine was added and the stirring continued. The mixture became viscous as the soap formed, and was allowed to cool. When it reached 10° C., the isopentane and mineral oil were added. The resulting gel was then stored at 4° C. until required for use.

EXAMPLE 5

The following microemulsion was made by the procedure of Example 4. It had a soap content of approximately 20%.

| Material | % w/w |
|---|---|
| Water | 60.73 |
| Palmitic acid | 10.57 |
| Triethanolamine | 7.69 |
| Coconut fatty acid | 7.5 |
| Mineral oil | 6 |
| Propylene glycol | 4.11 |
| Isopentane | 3 |
| Methyl paraben | 0.2 |
| Propyl paraben | 0.1 |
| Peg-150-distearate | 0.1 |

EXAMPLE 6

The following microemulsion was made by the procedure of Example 4. It had an organic liquid (mineral oil) content of 5%.

| Material | % w/w |
|---|---|
| Water | 61.73 |
| Palmitic acid | 10.57 |
| Triethanolamine | 7.69 |
| Coconut fatty acid | 7.5 |
| Mineral oil | 5 |
| Propylene glycol | 4.11 |
| Isopentane | 3 |
| Methyl paraben | 0.2 |
| Propyl paraben | 0.1 |
| Peg-150-distearate | 0.1 |

EXAMPLE 7

The following microemulsion was made by the procedure of Example 4. It had an organic liquid (mineral oil) content of 20%.

| Material | % w/w |
|---|---|
| Water | 46.73 |
| Palmitic acid | 10.57 |
| Triethanolamine | 7.69 |
| Coconut fatty acid | 7.5 |
| Mineral oil | 20 |
| Propylene glycol | 4.11 |
| Isopentane | 3 |
| Methyl paraben | 0.2 |
| Propyl paraben | 0.1 |
| Peg-150-distearate | 0.1 |

EXAMPLE 8

The following microemulsion was made by the procedure of Example 4. It had a volatile component (isopentane) content of 5%.

| Material | % w/w |
|---|---|
| Water | 58.73 |
| Palmitic acid | 10.57 |
| Triethanolamine | 7.69 |
| Coconut fatty acid | 7.5 |
| Mineral oil | 6 |
| Propylene glycol | 4.11 |
| Isopentane | 5 |
| Methyl paraben | 0.2 |
| Propyl paraben | 0.1 |
| Peg-150-distearate | 0.1 |

EXAMPLE 9

The following microemulsion was made by the procedure of Example 4. It had a volatile component level (isopentane) of 10%.

| Material | % w/w |
|---|---|
| Water | 53.73 |
| Palmitic acid | 10.57 |
| Triethanolamine | 7.69 |
| Coconut fatty acid | 7.5 |
| Mineral oil | 6 |
| Propylene glycol | 4.11 |
| Isopentane | 10 |
| Methyl paraben | 0.2 |
| Propyl paraben | 0.1 |
| Peg-150-distearate | 0.1 |

EXAMPLE 10

The following formulation was made by the procedure of Example 1. It had a water content of 50%.

| Material | % w/w |
|---|---|
| Water | 50 |
| Palmitic acid | 10.57 |
| Triethanolamine | 7.69 |
| Coconut fatty acid | 7.5 |
| Mineral oil | 15.73 |
| Propylene glycol | 4.11 |
| Isopentane | 4 |
| Methyl paraben | 0.2 |
| Propyl paraben | 0.1 |
| Peg-150-distearate | 0.1 |

The microemulsions of Examples 4 to 10 were very satisfactory pressure generators when confined in a closed space and allowed to warm up, eg. in ballpoint pens.

EXAMPLE 11

A pressure generating composition was made by dissolving or dispersing a gas in a grease. Gilugel CAO was mixed and cooled to 0° C. Isopentane was then added and the mixture stirred until homogeneous. It was then stored at 4° C. until required. As made, the mixture contained 94% by weight Gilugel CAO (from Giuline Chemie GmbH) and 6% by weight isopentane. The pressure developed from one gram of this formulation was measured with a Digitron manometer and found to be 3.8 psi.

EXAMPLE 12

Example 11 was repeated using Gilugel MIN in place of Gilugel CAO (in the same amount). The pressure from one gram of composition was measured with a Digitron manometer and found to be 3.8 psi.

EXAMPLE 13

The following example is of a water-in-oil emulsion pressure generating composition of the invention.

|  | % w/w |
|---|---|
| Gilugel MIN | 15 |
| Isopentane | 4 |
| Isostearyl diglycerol succinate | 5 |
| Mineral oil | 5 |
| Water | 70.7 |
| Methyl paraben | 0.2 |
| Propyl paraben | 0.1 |

Gilugel MIN, isostearyl diglycerol succinate and mineral oil were mixed together and heated to 80° C. Water, methyl paraben and propyl paraben were mixed together and heated to 80° C. The water phase was then added slowly to the oil phase and homogenised well. The resulting cream was cooled to below 10° C. The resulting composition was then stored at 4° C. until required.

The pressure generating compositions of Examples 11 to 13 were very satisfactory pressure generators when confined in a closed space and allowed to warm to ambient temperature, eg. in ballpoint pens as described herein.

This invention also relates to ballpoint pens and to inks therefor.

In a conventional ballpoint pen, a reservoir column of thick ink bears onto the rear side of the writing ball. As the ball is rotated in its seat, the thick ink in contact with the ball is conveyed on the ball surface to be deposited on the paper or other substrate. As ink is withdrawn, the reservoir column of ink will flow down to maintain contact with the ball. This is vital since, if contact is lost and the ink will not flow on its own to re-establish contact with the ball, the pen becomes useless.

In the early days of ballpoint pens, the inks were oil-based. They suffered a number of disadvantages including bleed into paper, point bleed (oil separation) and messiness. The subsequent introduction of dye-based glycol inks, which contained resins to reduce smearing and improve temperature stability, gave a major improvement in performance. Currently, most ballpoint pen inks are based on organic solvents such as phenyl glycols, diethylene glycol ethyl ether, dipropylene glycol or benzyl alcohol, or mixtures of two or more thereof.

There have recently been developed a family of aqueous pigmented inks many of which display bright and attractive colours. In order to provide these inks in ballpoint pens, the pigments have been formulated as aqueous suspensions containing a thickener such as xanthan gum, carageenan gum, guar gum, locust bean gum or hydroxyethyl cellulose. These suspensions show shear thinning and can serve as inks in ballpoint pens. However, in use, a number of problems arise. For example, the aqueous suspension does not lubricate the ball in its seat and, as a result, severe wear can occur over a period of use and the pens do not write very smoothly.

One of the most important requirements of a ballpoint pen ink is that it should write very smoothly. The organic-based ballpoint inks generally (but not invariably) write much more smoothly than the recently developed aqueous-based inks, but even the organic based inks are not always as smooth in use as would be desired, and in addition they have the disadvantage of being somewhat sticky.

We have now found a way of improving the smoothness of organic-based ballpoint pen inks. Furthermore, we have found a way of providing pigmented inks whereby smooth writing can be obtained as well as a reduced ball/seat wear as compared with known aqueous-based ballpoint pen inks. According to the present invention, we include a grease in a ballpoint pen ink.

In a first aspect, the invention provides an ink for a ballpoint pen, which ink comprises a dispersion of an organic solvent having a colorant dissolved therein and a grease.

The ink can be made by dispersing a grease in an organic solvent having a colorant dissolved therein. The grease can be preformed, or it may be made in situ by subjecting a mixture of its components (mobile phase and structural phase) to high shear.

According to this first aspect of the invention, ballpoint pen inks comprising a solution of a colorant in an organic solvent can be substantially improved by incorporating therein a grease. The grease promotes smoother writing. The presence of the grease will normally thicken the ink, but its presence imparts a shear thinning quality to the ink so that, under the high shear conditions around the ball (in use of the pen) the ink is thinned to provide an elastohydrodynamic layer usually about 500 nm thick on the ball. An elastohydrodynamic layer is a structured layer which deposits at the interface between two bodies despite the presence of high shear and compressive forces.

The nature of the organic solvent and the colorant are not critical. The solvent is preferably a phenyl glycol, diethylene glycol ethyl ether, dipropylene glycol, or benzyl alcohol, or any mixture of two or more thereof. The colorant can be any suitable ballpoint pen ink dye. We have found Solvent Blue 38, Basic Blue 7 and Solvent Violet 8 to be very suitable but other colorants can be used.

The nature of the grease is not critical. We prefer to use soap-based mineral oil greases, but other greases can be used. Preferably, the soap in the grease is a higher (i.e. $C_{12}$ and above) carboxylic acid salt of an alkali or alkaline earth metal, or an aluminium soap, an aluminium/magnesium mixed soap, or a complex soap. As stated, the preferred mobile phase is mineral oil, but castor oil and silicone oil greases, for example, can be used. It is also possible to use other greases such as perfluoropolyether greases, eg. Krytox® (from DuPont).

The preferred mineral oils for the greases are 65/75 mineral oil (i.e. oil of a viscosity from 65 to 75 centipoise) and oils from the Gravex series, eg. Gravex 21 (available from Shell Oils) and similar oils from the Enerthene series (available from BP Oil). Mineral oil soap based greases are, of course, commercially available (eg. Gilugel from Giulini GmbH) but they can be produced by melting the soap in the oil and then cooling, as is known in the art.

The amounts of the three main components of the ink are not particularly critical, but will usually be (in weight % based on the weight of the ink):

|  | general | preferred | most preferred |
|---|---|---|---|
| solvent | 20–90 | 30–70 | 40–60 |
| colorant | 5–60 | 15–50 | 20–45 |
| grease | 0.5–50 | 2–40 | 5–30 |

The inks of the invention can, of course, contain other ingredients as desired and as may be usual in the art.

The invention further includes a ballpoint pen or refill therefore wherein the ink is an ink of the invention. To be suitable as ballpoint pen inks, the inks of the invention are formulated with an appropriate viscosity (at least 500 centipoise) as will be well understood by those skilled in the art.

The use, in accordance with the present invention, of a grease in ballpoint pen inks has enabled the formulation of certain new ballpoint pen inks. These inks comprise a pigment suspended in grease, and they have proved very satisfactory ballpoint pen inks. In particular, they are very smooth in use, the grease lubricating the ball and providing an excellent suspension medium for the pigment.

Printing inks which comprise a pigment suspended in a grease (or in grease-forming components) are known from, for example, U.S. Pat. Nos. 1,237,126 and 5,158,606. In U.S. Pat. No. 1,237,126, a printing ink is made of an aluminium salt of a fatty acid, a hydrocarbon mineral oil and a pigment. The ink is used in roller printing. In U.S. Pat. No. 5,372,635, a printing ink is described which comprises a dispersion of a pigment in an oil and a tall oil fatty acid soap. The ink is especially for use in lithographic printing processes utilising tap water. These inks are not described as suitable for use in ballpoint pens nor would they be so since their viscosities would normally be well above the maximum acceptable in conventional ballpoint pens. Thus, the printing inks if placed in conventional ballpoint pens, would not write out because they would be too viscous.

The preferred ballpoint pigment ink of the present invention comprises a pigment, a grease, an organic liquid which is the same as the mobile phase of the grease or is compatible therewith, and a dispersant.

Any grease can be used but we prefer the mineral oil and other greases described hereinabove with reference to the first aspect of the invention. Reference should be made thereto for details.

The pigment inks of the invention can be made by dispersing a pigment in an organic liquid with a dispersant, adding a grease and mixing, the organic liquid being the same as the mobile phase in the grease or compatible therewith.

Alternatively, the inks can be made by dispersing a pigment in an organic liquid with a dispersant and the mobile phase and structural phase components of a grease; and subjecting the mixture to high shear to form the grease; wherein the organic liquid is the same as the mobile phase of the grease or is compatible therewith.

It is preferred that the organic liquid be the same as the mobile phase of the grease. If it is not identical, then it should certainly be compatible therewith. By "compatible therewith" we mean that once the grease and organic liquid are mixed, the mixture is stable and the microstructure of the grease is intact, for example, if a mineral oil grease is used, a compatible organic liquid could be a different mineral oil.

The amounts of the components of the pigment inks of the invention can vary widely. Generally, however, the amounts will by (by weight of the ink):

|  | general | preferred | most preferred |
|---|---|---|---|
| grease | 0.5–80 | 2–50 | 5–25 |
| organic liquid | 10–85 | 30–80 | 45–75 |
| pigment | 1–50 | 5–40 | 15–30 |
| dispersant | 0.1–5 | 1–3 | 1.5–2.5 |

In order to disperse the pigment in the grease and to provide a stable dispersion, it will usually be necessary to use one or more dispersants. Suitable dispersants will be soluble in the organic liquid or mobile phase and will thus normally contain a long chain hydrocarbon moiety, e.g. a stearyl or oleyl group with a functional head group. As the functional head group, the dispersants can, for example, have polyol derivatives such as glycerol or sorbitan derivatives, to provide the appropriate polarity to bind to the pigment. Suitable dispersants will be well known to those skilled in the art. We prefer to use Solsperse hyperdispersants eg. Solsperse 13940, and Solsperse 17000, optionally with Solsperse 5000 from Zeneca ("Solsperse" is a trademark). The effectiveness of Solsperse 17000 is significantly improved by the use therewith of Solsperse 5000 as a synergist. Solsperse 5000 is essentially a pigment derivative that has a strong affinity for the particular pigment type and furnishes the surface with anchoring sites for the conventional polymeric Solsperse hyperdispersant. The amount of dispersant will vary depending on the system in which it is used, but the total amount will normally not exceed about 5% by weight of the ink.

The pigments used in the inks of the invention must be of small particle size to prevent clogging of the pen ball. We prefer to use printing ink pigments which in use form a colloid or sol. In general, the pigment size should not be greater than 5 $\mu$m, preferably 0.1 to 2.0 $\mu$m, most preferably 0.2 to 1.0 $\mu$m. In the manufacture of the inks of the invention, we prefer to treat the final ink to remove any particulate agglomeration. This may be done, for example, by suitably processing the ink in a triple mill or by filtering. Filtration can be effected, for example, with a stainless steel unit equipped with 5 to 30 micrometer pads. The unit is connected to an air line with maximum pressure of about 70 psi (480 kPa). The selection of pad size and the pressure will depend on the filtration speed desired and the pigment particle size.

Whilst the nature of the pigment is not critical, we prefer to use pigments designed for use in organic solvents, eg. BASF's Heliogen or Paliotol series pigments.

The pigment inks of the invention are loaded into ballpoint pens or refill reservoirs in conventional manner. Thus, for example, 1 g of a pigment ink of the invention is injected into the reservoir barrel using a syringe and an appropriate dispensing needle. The ball point is fitted and the pen (or refill) is then placed point down in a centrifuge set at 4000 rpm for 5 minutes. This ensures that there is no gap between the column of ink and the back of the ball.

The inks of the invention can be used in the same way as conventional ballpoint pen inks or they can be used in a reservoir containing a pressure generating composition. In this arrangement, the ink is loaded in a conventional reservoir above a conventional ball, and then a pressure generating composition is provided above the ink. The reservoir is then closed and the composition generates a gas pressure on the ink column to maintain it continuously in good contact with the ball.

The pressure generating composition used with a grease ink should preferably be aqueous based so as to be immiscible with the grease ink of the invention. If an organic-based composition is used, then a barrier may be provided between the ink and the pressure generating material, in order to prevent contact therebetween.

The use of a pressure generating composition with the inks of the present invention makes it possible to dispense the inks reliably from the reservoir without the need for a high pressure permanent gas. This enables the reservoir to be manufactured more cheaply, because it does not need to withstand such high pressures. In addition, the reservoir does not need to be pressurised during the manufacturing process: the ink and the pressure generating material can be placed in the reservoir at atmospheric pressure, using conventional manufacturing methods, and then the reservoir can be sealed. After sealing, the reservoir pressure will build up, over time, to the required working pressure. Whilst the actual time will depend on all the circumstances, it will normally be a matter of minutes, e.g. from 8 to 12 minutes.

Figure 4:
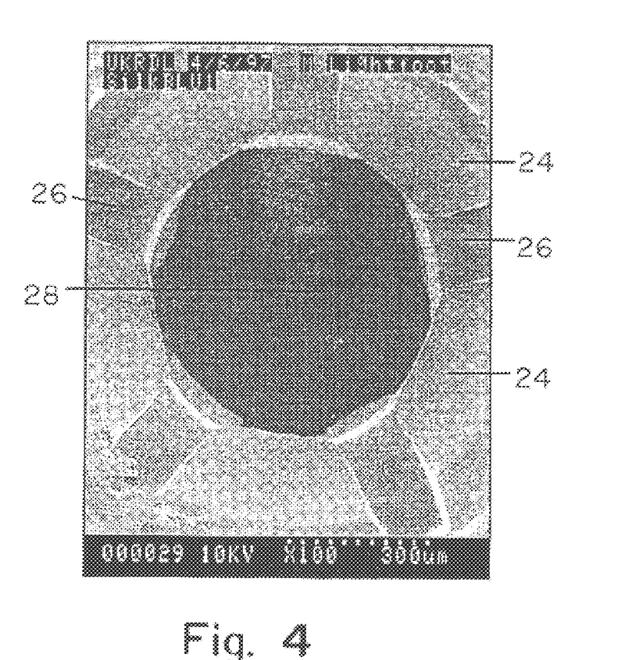
FIG. 4 is an SEM photograph of a ballpoint pen ball seat with the ball removed, the pen being loaded with an ink of the invention.
Figure 5:
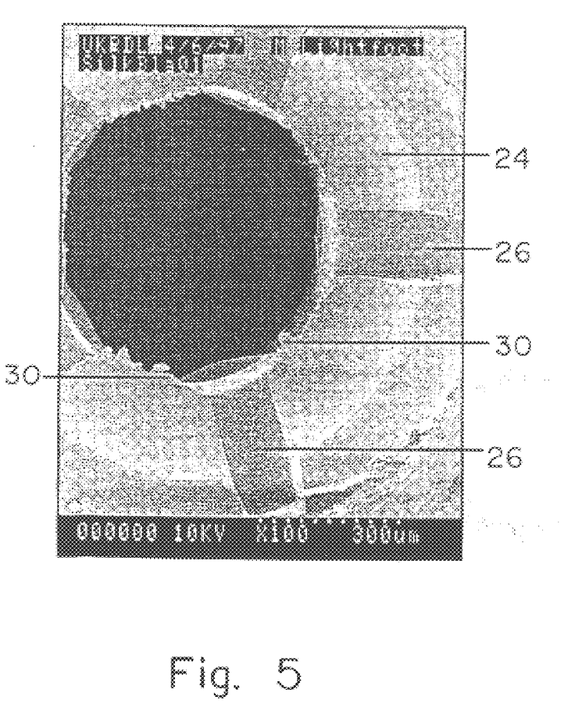
FIG. 5 is an SEM photograph of a ballpoint pen ball seat with the ball removed, the pen being loaded with an ink not in accordance with the invention.

Referring now to FIGS. 4 and 5 of the drawings, in which like numerals indicate like parts, there is shown an SEM photograph taken axially of the ball seat of a ballpoint pen, the ball having been removed. The ball seat comprises a concave cup-shaped member 24 having five radial grooves 26 therein equispaced around the member 24. Centrally of member 24 is an orifice 28 which communicates with the ink reservoir and with grooves 26 to feed ink thereto.

The ball (not shown) seats on the cup-shaped member 24. In use of the pen, ink flows out of orifice 28 into grooves 26. The ball contacts the ink supplied in the grooves 26 and, as the ball is rotated in use, as the ball is rotated in use, ink passes onto its surface and is laid on the paper or other substrate on which the ball is rolled. Small quantities of ink will also pass onto concave cup-shaped member 24 to lie thereon between the ball and the cup-shaped member surface, thus lubricating the ball/seat. The ball is held in its seat on the cup-shaped member 26 by a top rim not shown but which will be well understood in the art.

FIG. 4 shows a pen in which the cup-shaped member 24 is of nickel silver and which had been written with for 2200 m. The reservoir of the pen contained an ink of the invention of the following composition:

| | |
|---|---|
| Diethylene glycol ethyl ether | 4.87 g |
| 2-Phenoxyethanol | 4.87 g |
| Dipropylene glycol | 2.41 g |
| Oleic acid | 0.48 g |
| Resin PVP-90 (ex. BASF) | 0.073 g |
| Solvent Violet 8 | 1.18 g |
| Basic Blue 7 | 1.30 g |
| Solvent Blue 38 | 7.66 g |
| Gilugel Min | 2.74 g |

The pen of FIG. 5 is identical to that of FIG. 4 and had also been written for 2200 m. However, the ink in the FIG. 5 pen was an ink of the following composition:

| | |
|---|---|
| Diethylene glycol ethyl ether | 5.05 g |
| 2-Phenoxyethanol | 5.05 g |
| Dipropylene glycol | 2.5 g |
| Oleic acid | 0.5 g |
| Resin SK | 3.43 g |
| Resin PVP-90 (ex-BASF) | 0.08 g |

| -continued | |
|---|---|
| Solvent Violet 8 | 0.98 g |
| Basic Blue 7 | 1.08 g |
| Solvent Blue 38 | 6.35 g |

Thus, the ink used in the FIG. 5 pen did not contain any grease.

As can be seen in FIG. 5, the surface of cup-shaped member 24 adjacent the orifice 28 is severely worn with the formation of burrs, e.g. at regions 30. However, no such damage can be seen in the pen of FIG. 4. The absence of such damage in FIG. 4 is due to the presence in the ink of the grease. The ink of the invention forms an elastohydrodynamic layer between the ball and the seat, so reducing or even eliminating any significant damage in use of the pen. This manifests itself to the user as very smooth writing over the life of the pen.

EXAMPLE 14

Mineral oil 65/75 (20 g) and a dispersant Solsperse 17000 (1.40 g) were mixed for 10 min. in a high speed shearing mixer. A synergist (Solsperse 5000 (0.16 g)) was added and the mixing continued for a further 10 min. A pigment, BASF Heliogen blue D 7084 DD (9.35 g) was then added and mixed for 10 hours to ensure effective dispersion. The vessel was then placed in a water bath at 70° C. and a mineral oil grease Gilugel MIN (9 g) and mineral oil 65/75 (8.2 g) were added and mixed for 2 hours using the same high speed shearer. (Gilugel MIN is available from Giulini Chemie GmbH, Germany, and is a grease formed from mineral oil and aluminium magnesium hydroxide stearate as the soap.)

The resulting ink was loaded into the elongate barrel reservoir of a ballpoint pen, having a ball tip at the lower end. A plug of pressure generating composition gel was then placed above the ink in the reservoir and the reservoir crimped to seal it closed at the upper end. The gel was as prepared in Example 16 hereafter.

The pen wrote very smoothly with excellent ink lay down. After extended use, there was no evidence of any discontinuity in the ink column which remained in excellent contact with the ball.

EXAMPLE 15

A commercially available dispersion (10 g) of a black pigment in mineral oil ("Gravex 21", available from Industrial Dispersions Ltd. of Manningtree, Essex) was mixed with mineral oil grease Gilugel MIN (10 g) at room temperature using an Ultra Turrax 25 high speed stirrer. Stirring was continued for 30 minutes. The resulting ink of the invention was placed in a ball-point pen as described in Example 14. A plug of the pressure generating composition was also used as in Example 14. The resulting pen functioned very well.

EXAMPLE 16

A pressure generating composition was made of the following components:

|  | wt. % |
| --- | --- |
| Palmitic acid | 10.57 |
| Triethanolamine | 7.69 |
| Coconut fatty acid | 7.5 |
| Mineral oil | 6 |
| Propylene glycol | 4.11 |
| Isopentane | 4 |
| Methyl paraben | 0.2 |
| Propyl paraben | 0.1 |
| Water | 59.83 |

The water used in the composition was first heated to 95° C. to remove air therefrom.

All the fatty acids and the propylene glycol, methyl paraben, propyl paraben and water were placed in a vessel and heated with stirring under a vacuum to 75° C. With the mixture at this temperature, the triethanolamine was added and the stirring continued. The mixture became viscous as the soap formed, and was allowed to cool. When it reached 20° C., the isopentane and mineral oil were added. Cooling was continued to 10° C. with slow stirring. The resulting gel was stored below 10° C. until required for use.

Further compositions were made in which the amount of mineral oil was varied up to 16% and the amount of isopentane was varied up to 10%, the volume of water being adjusted accordingly q.s. 100%.

All the compositions were very satisfactory as pressure generators when confined in a closed space and allowed to warm to ambient temperature (e.g. about 20° to 25° C.). In particular, they were satisfactory when used as small plugs in ballpoint pen ink reservoirs containing inks of the present invention.

EXAMPLE 17

A ballpoint pen ink according to the invention was made from:

Papermate Blue Ballpen Ink (28.8 g)

2-phenoxyethanol>99% (3.00 g) from Fluka

Gilugel MIN (6.90 g) from Giulini Chemie GmbH.

The ink was placed in a 50 ml beaker and the 2-phenoxyethanol was added. An Ultra-Turrax T25 mixer was lowered into the beaker to just above the bottom. Thin plastic film was wrapped around the beaker and the stirrer to reduce evaporation, and the mixture was stirred at 8000 rpm for one hour. During this time, the mixture became warm.

At the end of the one hour, the Gilugel MIN was added and the mixture stirred at the same speed for a further 4 hours to form the ballpoint pen ink.

A reservoir tube was filled with ink (about 1 ml) by syringing air from one end of the tube. The tube was then centrifuged at 3000 g for 10 minutes to remove any entrapped air. Then, a ballpoint was firmly attached to one end of the tube and a quantity (about 1.5 cm in length) of a pressure generating composition was syringed into the open end of the tube. Finally, the open end of the tube was firmly closed with a size 5 bung.

In use of the pen, the ink flowed very smoothly and provided excellent lay down, even when used upside down, without any discontinuity in the writing.

The pressure generating composition was made up of:

| Water | 58.14% |
| --- | --- |
| Triethanolamine | 7.69% |
| Coconut fatty acid | 7.5% |
| Hampsoyl L | 11.16% |
| PEG 150 distearate | 0.1% |
| Empilan MAA | 2.0% |
| Isopentane | 3.0% |
| Mineral oil | 6.0% |
| Propylene glycol | 4.11% |
| Methyl paraben | 0.2% |
| Propyl paraben | 0.1% |

The pressure developed from this formulation was 4.8 psi.

EXAMPLE 18

A ballpoint pen ink according to the invention was made from:

| Papermate blue ballpen ink | 19.64 g | |
| --- | --- | --- |
| 2-Phenoxyethanol | 2.01 g | |
| Gilugel SIL5 | 4.74 g | (from Giuline Chemie GmbH) |

The ballpen ink and 2-phenoxyethanol were stirred at 8000 rpm for 1 hour using an Ultra-Turrax T25 high shear mixer. Gilugel SIL5 was added and the mixing continued for 4 hours, external cooling being applied to the mixing vessel. The resulting ink of the invention (viscosity 50,000 cpoise) was placed in a ballpoint pen as described in Example 17. A plug of the pressure generating composition was also used as in Example 17. The ballpoint pen wrote extremely smoothly. (Gilugel SIL5 is a mineral oil based grease with aluminium-magnesium hydroxide stearate soap as thickener).

EXAMPLE 19

A ballpoint pen ink according to the invention was made from:

| Papermate blue ballpen ink | 10 g | |
| --- | --- | --- |
| 2-Phenoxyethanol | 2 g | |
| Albida R2 | 2.12 g | (from Shell U.K. Ltd) |

The Albida R2 was added to the ballpen ink and stirred at 8000 rpm using an Ultra-Turrax T25 high shear mixer. 2-Phenoxyethanol was added immediately and stirring continued for 2 hours. The resulting ink of the invention (viscosity 40,000 c poise) was placed in a ballpoint pen as described in Example 17. The pen wrote smoothly either with or without addition of the plug of pressure generating composition as described in Example 17. (Albida R2 is a mineral oil based grease with a lithium hydroxystearate complex soap as thickener.)

EXAMPLE 20

A ballpoint pen ink according to the invention was made from:

| Papermate black ballpoint ink | 19.61 g | |
| 2-Phenoxyethanol | 2.0 g | |
| Gilugel Min | 4.73 g | (from Giulini Chemie GmbH) |

The ballpen ink and 2-phenoxyethanol were stirred at 8000 rpm for 1 hour using an Ultra-Turrax T25 high shear mixer. Gilugel Min was added and the mixing continued for 4 hours, external cooling being applied to the mixing vessel. The resulting ink of the invention was placed in a ballpoint pen as described in Example 17. A plug of the pressure generating composition was also used as in Example 17. The ballpoint pen wrote extremely smoothly. (Gilugel Min is a mineral oil based grease with aluminium-magnesium hydroxide stearate soap as thickener.)

EXAMPLE 21

A ballpoint pen ink according to the invention was made from:

| Papermate blue ballpen ink | 19.6 g |
| --- | --- |
| 2-Phenoxyethanol | 2.0 g |
| Aluminium-Magnesium Hydroxide stearate | 0.94 g |
| 65/75 Mineral Oil | 3.7 g |

The ballpen ink, 2-phenoxyethanol and aluminium-magnesium hydroxide stearate were stirred at 8000 rpm for 1 hour using an Ultra-Turrax T25 high shear mixer. External cooling was applied. Mineral oil was added and the mixing continued for 5 hours. The resulting ink of the invention was placed in a ballpoint pen as described in Example 17. A plug of the pressure generating composition was also used as in Example 17. The ballpoint pen wrote extremely smoothly.

EXAMPLE 22

A ballpoint pen ink according to the invention was made from:

| Diethylene glycol ethyl ether | 4.87 g |
| --- | --- |
| 2-Phenoxyethanol | 4.87 g |
| Dipropylene glycol | 2.41 g |
| Oleic acid | 0.48 g |
| Resin PVP-90 (ex-BASF) | 0.073 g |
| Solvent Violet 8 | 1.18 g |
| Basic Blue 7 | 1.30 g |
| Solvent Blue 38 | 7.66 g |
| Gilugel Min | 2.74 g |

The combined solvents were stirred at 75° C. Resin was added and, when dissolved, the dyes were introduced to the mixture. Stirring was continued for 2 hours at 75–80° C. after which time the ink was allowed to cool. Gilugel Min was added and the mixture stirred at 8000 rpm for 4 hours using an Ultra-Turrax T25 high shear mixer, external cooling being applied to the mixing vessel. The resulting ink of the invention (viscosity 12000 cpoise) was placed in a ballpoint pen as described in Example 17. The pen wrote smoothly either with or without addition of the plug of pressure generating composition as described in Example 17.

EXAMPLE 23

A ballpoint pen ink according to the invention was made from:

| Diethylene glycol ethyl ether | 4.38 g |
| --- | --- |
| 2-Phenoxyethanol | 4.38 g |
| Dipropylene glycol | 2.17 g |
| Oleic acid | 0.43 g |
| Resin PVP-90 (ex-BASF) | 0.065 g |
| Solvent Violet 8 | 1.06 g |
| Basic Blue 7 | 1.17 g |
| Solvent Blue 38 | 6.88 g |
| Gilugel Min | 4.93 g |

The combined solvents were stirred at 75° C. Resin was added and, when dissolved, the dyes were introduced to the mixture. Stirring was continued for 2 hours at 75–80° C. after which time the ink was allowed to cool. Gilugel Min was added and the mixture stirred at 8000 rpm for 4 hours using an Ultra-Turrax T25 high shear mixer, external cooling being applied to the mixing vessel. The resulting ink of the invention (viscosity 50000 cpoise) was placed in a ballpoint pen as described in Example 17. A plug of the pressure generating composition was also used as in Example 17. The ballpoint pen wrote extremely smoothly.

EXAMPLE 24

A ballpoint ink according to the invention was made from:

| Heliogen blue D 7084DD | 2.44 g | ex-BASF |
| --- | --- | --- |
| 65/75 Mineral oil | 7.36 g | |
| Solsperse 17000 | 0.7 g | |
| Solsperse 5000 | 0.021 g | |
| Gilugel CAO | 2.3 g | |

The mineral oil and dispersant Solsperse 17000 were stirred at 8000 rpm for 10 minutes using an Ultra-Turrax T25 high shear mixer. Synergist Solsperse 5000 was then added and stirring continued for a further 10 minutes. Pigment was then added over 20 minutes with minimal stirring, and then the mixture stirred for a further 10 hours at high shear. Gilugel CAO was then added and stirring continued for 2 hours. The resulting ink of the invention (viscosity 10,000 cpoise) was placed in a ballpoint pen as described in Example 17. The pen wrote smoothly either with or without addition of the plug of pressure generating composition as described in Example 17.

EXAMPLE 25

A ballpoint pen ink according to the invention was made from:

| Heliogen blue D 7084DD | 2.44 g | ex-BASF |
| --- | --- | --- |
| 65/75 Mineral oil | 7.36 g | |
| Solsperse 17000 | 0.7 g | |
| Solsperse 5000 | 0.021 g | |
| Gilugel Min | 1.0 g | |

The mineral oil and dispersant Solsperse 17000 were stirred at 8000 rpm for 10 minutes using an Ultra-Turrax T25 high shear mixer. Synergist Solsperse 5000 was then added and stirring continued for a further 10 minutes. Pigment was then added over 20 minutes with minimal stirring, and then the mixture stirred for a further 10 hours at high shear. Gilugel Min was then added and stirring continued for 2 hours. The resulting ink of the invention (viscosity 20,000 cpoise) was placed in a ballpoint pen as described in Example 17. The pen wrote smoothly either with or without addition of the plug of pressure generating composition as described in Example 17.

EXAMPLE 26

A ballpoint pen ink according to the invention was made from:

| | | |
|---|---|---|
| Heliogen blue D 7084DD | 2.44 g | ex-BASF |
| 65/75 Mineral oil | 9.2 g | |
| Solsperse 17000 | 0.7 g | |
| Solsperse 5000 | 0.021 g | |
| Aluminium magnesium hydroxide stearate | 0.46 g | |

The mineral oil and dispersant Solsperse 17000 were stirred at 8000 rpm for 10 minutes using an Ultra-Turrax T25 high shear mixer. Synergist Solsperse 5000 was then added and stirring continued for a further 10 minutes. Pigment was then added over 20 minutes with minimal stirring, and then the mixture stirred for a further 10 hours at high shear. Aluminium magnesium hydroxide stearate was then added and stirring continued for 1 hour. The resulting ink of the invention (viscosity 20,000 cpoise) was placed in a ballpoint pen as described in Example 17. The pen wrote smoothly either with or without addition of the plug of pressure generating composition as described in Example 17.

EXAMPLE 27

A ballpoint pen ink according to the invention was made from:

| | |
|---|---|
| Carbon black | 7.44 g |
| 65/75 Mineral oil | 28.2 g |
| Solsperse 13940 | 0.45 g |
| Gilugel Min | 4.5 g |

The mineral oil and dispersant Solsperse 17000 were stirred at 8000 rpm for 10 minutes using an Ultra-Turrax T25 high shear mixer. Carbon black was added and stirring continued at 25° C./30 minutes and 70° C./3.5 hours. Gilugel Min was added and stirring continued for 1.5 hours. The resulting ink of the invention (viscosity 40000 cpoise) was placed in a ballpoint pen as described in Example 17. A plug of the pressure generating composition was also used as in Example 17. The ballpoint pen wrote smoothly.

What is claimed is:

1. The use of a pressure generating composition capable of releasing a volatile component to generate a pressure, to aid the dispensation of a fluid from a reservoir without the said composition itself being dispensed, wherein the pressure generating composition comprises an oil-in-water or water-in-oil microemulsion, or a siloxane or hydrocarbon grease, or an elastomer, containing said volatile component.

2. The use according to claim 1, wherein the fluid is a paste, gel or liquid.

3. The use according to claim 2, wherein the fluid is an ink, and the reservoir is part of a writing implement.

4. The use according to claim 3, wherein the writing implement is a ballpoint pen.

5. The use according to claim 1, wherein the microemulsion comprises mineral oil dispersed in an aqueous soap solution, and wherein the volatile component is in the oil.

6. A dispenser for dispensing a fluid, which dispenser comprises a reservoir adapted to contain a fluid, the reservoir having an outlet through which said fluid can be dispensed, and a pressure generating composition capable of releasing a volatile component to generate a pressure within the reservoir to aid dispensation of the fluid, wherein said composition is capable of releasing the volatile component as the fluid is dispensed, in order to maintain the pressure in the reservoir at a level sufficient to aid dispensation of the fluid, and wherein the said composition is not dispensed with the fluid, said pressure generating composition comprising a water-in-oil or oil-in-water microemulsion or a siloxane or hydrocarbon grease, or an elastomer, containing said volatile component.

7. A dispenser according to claim 6 wherein said reservoir contains a fluid.

8. A dispenser according to claim 7, wherein the pressure in the reservoir is above about 105 kPa.

9. A dispenser according to claim 7, wherein the pressure generating composition is immiscible with the fluid.

10. A dispenser according to claim 7, wherein the pressure generating composition is separated from the fluid by a barrier.

11. A dispenser according to claim 10, wherein the pressure generating composition is confined in an expansible container in the reservoir, and separated thereby from said fluid.

12. A dispenser according to claim 7, wherein the pressure generating composition is a microemlsion which is in the form of a gel.

13. A dispenser according to claim 7, wherein the pressure generating composition is a microemulsion which comprises an oil-in-water microemulsion, wherein the volatile component is in the oil.

14. A dispenser according to claim 13, wherein the oil is a mineral or vegetable oil or a synthetic oil, dispersed in an aqueous solution of a soap or a sarcosinate.

15. A dispenser according to claim 7, wherein the volatile component is a non-permanent gas.

16. A dispenser according to claim 15, wherein the volatile component is a saturated aliphatic hydrocarbon having from 4 to 6 carbon atoms, or a partially or wholly halogenated hydrocarbon.

17. A dispenser according to claim 16, wherein the volatile component is isopentane.

18. A dispenser according to claim 7, wherein the fluid is a paste, gel or liquid.

19. A dispenser according to claim 18, wherein the fluid is an ink and the dispenser is a writing implement or an ink refill therefor.

20. A writing implement or ink refill therefor, which comprises a dispenser according to claim 18, wherein the reservoir has an ink outlet, the implement or refill further comprising a tip adapted to deliver ink onto a surface, the reservoir and the tip being in fluid communication whereby ink can be fed from the reservoir to the tip.

21. A writing implement or ink refill therefor according to claim 20, wherein said tip comprises a ball.

22. A writing implement or ink refill therefor according to claim 21, which pen or refill contains an ink comprising a suspension of a pigment in a grease.

23. A writing implement or ink refill according to claim 22, wherein the ink comprises a pigment, a grease, an organic liquid which is the same as the mobile phase of the grease or is compatible therewith, and a dispersant.

24. A writing implement or ink refill according to claim 22, wherein the grease is a soap-based grease.

25. A writing implement or ink refill according to claim 24, wherein the soap in the grease is a higher carboxylic acid salt of an alkali or alkaline earth metal, or an aluminium soap, an aluminium/magnesium mixed soap, or a complex soap.

26. A writing implement or ink refill according to claim 24, wherein the grease is a mineral oil, castor oil or silicone oil grease.

27. A writing implement or ink refill according to claim 22, wherein the grease is a perfluoropolyether grease.

28. A writing implement or ink refill according to claim 22, wherein the amount of pigment in the ink is from 1 to 50% by weight.

29. A writing implement or ink refill according to claim 28, wherein the amount of pigment in the ink is from 15 to 30% by weight.

30. A writing implement or ink refill according to claim 22, wherein the pigment is a printing ink pigment.

31. A writing implement or ink refill according to claim 30, wherein the pigment is in the form of a colloid or a sol.

32. A writing implement or ink refill according to claim 22, wherein the ink includes at least one dispersant.

33. A writing implement or ink refill according to claim 21, which writing implement or ink refill contains an ink which comprises a suspension of pigment particles in a mixture of a mineral oil-based grease, mineral oil and a dispersant.

34. A writing implement or ink refill according to claim 21, which writing implement or ink refill contains an ink which comprises a dispersion of an organic solvent having a colorant dissolved therein and a grease.

35. A writing implement or ink refill according to claim 34, wherein the organic solvent comprises a phenyl glycol, diethylene glycol ethyl ether, dipropylene glycol, or benzyl alcohol, or any mixture of two or more thereof.

36. A writing implement or ink refill according to claim 34, wherein the grease is a soap-based grease.

37. A writing implement or ink refill according to claim 36, wherein the soap in the grease is a higher carboxylic acid salt of an alkali or alkaline earth metal, or an aluminium soap, an aluminium/magnesium mixed soap, or a complex soap.

38. A writing implement or ink refill according to claim 36, wherein the grease is a mineral oil, castor oil or silicone oil grease.

39. A writing implement or ink refill according to claim 34, wherein the grease is a perfluoropolyether grease.

40. A writing implement or ink refill according to claim 34, wherein the amount of grease is from 0.5% to 50% by weight, the amount of colorant is from 50% to 60% by weight and the amount of organic solvent is from 20% to 90% by weight.

41. A writing implement or ink refill according to claim 40, wherein the amount of grease is from 2 to 40% by weight, the amount of colorant is from 20% to 50% by weight, and the amount of organic solvent is from 40% to 60% by weight.

42. A dispenser according to claim 18, wherein the fluid is shaving soap or a shaving aid and the dispenser is part of a wet shaving system.

43. A wet shaving system which comprises a dispenser according to claim 42.

* * * * *